(12) United States Patent
Storey et al.

(10) Patent No.: US 7,914,768 B2
(45) Date of Patent: Mar. 29, 2011

(54) STABILISER FOR RADIOPHARMACEUTICALS

(75) Inventors: Anthony E. Storey, Amersham (GB);
Georg Brauers, Amersham (GB);
Koichi Hanaoka, Sodegaura (JP);
Yoshihito Minosako, Sodegaura (JP);
Koichi Homma, Sodegaura (JP);
Yoshifumi Shirakami, Sodegaura (JP)

(73) Assignees: GE Healthcare Limited, Buckinghamshire (GB); Nihon Medi-Physics, Co., Ltd., Hyogo (JP)

( * ) Notice: Subject to any disclaimer, the term of this patent is extended or adjusted under 35 U.S.C. 154(b) by 927 days.

(21) Appl. No.: 10/296,952

(22) PCT Filed: Jun. 18, 2001

(86) PCT No.: PCT/GB01/02652
§ 371 (c)(1),
(2), (4) Date: Oct. 21, 2004

(87) PCT Pub. No.: WO01/97862
PCT Pub. Date: Dec. 27, 2001

(65) Prior Publication Data
US 2005/0063902 A1    Mar. 24, 2005

(30) Foreign Application Priority Data
Jun. 22, 2000  (GB) .................................. 0015242.1

(51) Int. Cl.
*A61K 51/00* (2006.01)
*A61M 36/14* (2006.01)
(52) U.S. Cl. ..................... 424/1.77; 424/1.11; 424/1.65; 206/223; 206/569
(58) Field of Classification Search ................. 424/1.11, 424/1.37, 1.49, 1.65, 1.69, 1.73, 1.81, 1.85, 424/1.89, 9.1, 1.77; 534/7, 10–14; 206/223, 206/569, 570
See application file for complete search history.

(56) References Cited

U.S. PATENT DOCUMENTS

| | | | |
|---|---|---|---|
| 4,451,451 A * | 5/1984 | Rimmer ...................... 424/1.65 |
| 4,615,876 A * | 10/1986 | Troutner et al. ................. 534/14 |
| 4,642,229 A | 2/1987 | Cumming et al. |
| 5,093,105 A | 3/1992 | Flanagan et al. |
| 5,175,343 A * | 12/1992 | Fritzberg et al. .............. 560/145 |

FOREIGN PATENT DOCUMENTS

| | | |
|---|---|---|
| EP | 0 250 966 A | 1/1988 |
| EP | 0 508 724 A | 10/1992 |
| WO | WO87/01289 | 3/1987 |

OTHER PUBLICATIONS

S. J. Mathers, et al. "Reduction-Mediated Technetium-99M Labeling of Monoclonal Antibodies" Journal of Nuclear Medicine vol. 31, No. 5, 1990 pp. 692-697.
A. Morales, et al. "Freeze-dried formulation for the direct 99m-Tc-labeling of ior egf/r3 monoclonal antibody: Equivalence studies" Biotecnologia Aplicada vol. 17, No. 1, Jan. 1, 2000 pp. 39-44.
K. Schomacker, et al. "Verschiedene 99mTc-Generatoreluate: Auswirkungen auf die radiochemische Reinheit der Markierungsprodukte" Nuklearmedizin, Feb. 1994, vol. 33, No. 1 pp. 33-39.
B. Cleynhens, et al. "Evaluation of the efficacy of different antioxidants in technetium 99m-methylenediphosphonic acid preparations" Nuklearmedizin, Suppl., 1991, vol. 27 pp. 133-135.
D. E. Heggli, et al. "Differences in biodistribution in rats injected with 99m-Tc-MDP preparations with different stabilizing agents" European Journal of Nuclear Medicine 1988, vol. 14, No. 2 pp. 105-107.
J. Godard, et al. "Traitement de l'oedeme cerebral peritumoral par le tetracosactide" La Presse Medicale, May 15, 1993, vol. 22, No. 17 pp. 806-810.

* cited by examiner

Primary Examiner — D. L Jones

(57) ABSTRACT

A stabilized radiopharmaceutical composition, a kit including same, and a method for making same, where the radiopharmaceutical is (i) susceptible to either reductive degradation or radiolysis and which includes a metal complex of a radionuclide with a ligand, (ii) a first stabilizer for the radiopharmaceutical which is an amino-substituted aromatic carboxylic acid or a salt, ester or amide thereof, and (iii) a second stabilizer for the radiopharmaceutical which is a diphosphonic acid or salt thereof. The first and second stabilizers are present in an amount effective to stabilize the radiopharmaceutical, and the radiopharmaceutical is not a metal complex of the diphosphonic acid.

13 Claims, 1 Drawing Sheet

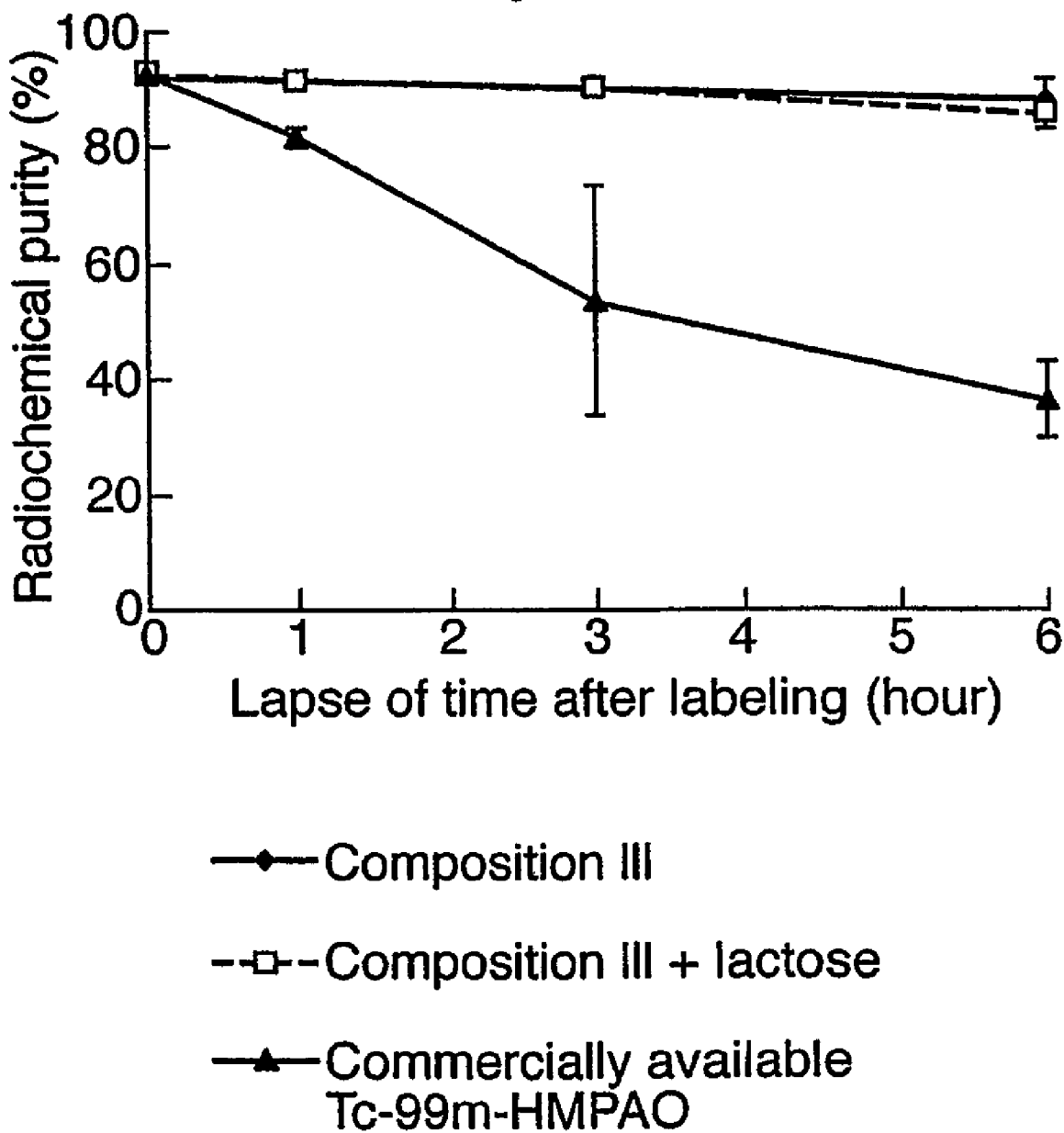

STABILISER FOR RADIOPHARMACEUTICALS

This application claims priority to international application number PCT/GB01/02652 filed Jun. 18, 2001 and also to patent application number 0015242.1 filed in Great Britain on Jun. 22, 2000.

FIELD OF THE INVENTION

The present invention relates to a stabilised radiopharmaceutical composition, together with non-radioactive kits for the preparation of the stabilised radiopharmaceutical composition.

BACKGROUND TO THE INVENTION

Some radiopharmaceuticals undergo decomposition due to either radiolysis or redox reactions, and hence exhibit undesirable instability. Non-radioactive kits for the preparation of radiopharmaceuticals, especially Tc-99m radiopharmaceuticals, may suffer from two types of instability:
(i) shelf-life instability of the non-radioactive composition over time,
(ii) instability of the radiopharmaceutical post-formation.
In the case of Tc-99m, the latter is referred to as post-reconstitution instability. U.S. Pat. No. 4,451,451 discloses that para-aminobenzoic acid (pABA) and analogues are useful stabilisers for technetium non-radioactive kits, including kits for the preparation of $^{99m}$Tc-complexes of diphosphonic acids.

Tc-99m-hexamethylpropyleneamine oxime (referred to hereinafter as $^{99m}$Tc-HMPAO), is a radiopharmaceutical commercially available as a regional cerebral blood flow imaging agent. $^{99m}$Tc-HMPAO is particularly unstable with respect to post-reconstitution stability. $^{99m}$Tc-HMPAO is usually prepared from a lyophilised, non-radioactive kit which contains HMPAO and stannous ion. The function of the stannous ion is to reduce the $^{99m}$Tc-pertechnetate ($^{99m}$TcO$_4^-$), ie. technetium in oxidation state Tc(VII), to the Tc(V) oxidation state of the $^{99m}$Tc-HMPAO metal complex. The radiochemical purity (Rcp) of $^{99m}$Tc-HMPAO one hour after Tc-99m labelling is only about 80%, so that it must be used within 30 minutes of $^{99m}$Tc labelling.

After Tc-99m radiolabelling, the Rcp of $^{99m}$Tc-HMPAO decreases with time due to the growth of three different radioactive impurities, namely: a hydrophilic secondary $^{99m}$Tc complex of unknown structure derived from $^{99m}$Tc-HMPAO, $^{99m}$Tc-pertechnetate ($^{99m}$TcO$_4^-$) and reduced-hydrolysed-technetium [$^{99m}$Tc]. Of these impurities, both the secondary complex and $^{99m}$Tc-pertechnetate are decomposition products of $^{99m}$Tc-HMPAO; however, it is reported that the decomposition mechanisms are different (J. Nucl. Med. 29, 1568-1576, 1988).

The secondary complex is believed to be produced when the lipophilic $^{99m}$Tc-HMPAO complex is exposed to excess unoxidised tin(II) (ie. stannous) remaining from the pertechnetate reduction step. On the other hand, the $^{99m}$Tc-pertechnetate impurity is produced when $^{99m}$Tc-HMPAO and the secondary complex are oxidised by the free radicals produced in solution by the action of radiation, ie. radiolysis of the solvent.

Accordingly, in order to inhibit the production of both the $^{99m}$Tc-pertechnetate and secondary complex impurities, the addition of stabilisers has been disclosed. Thus, Nucl. Med. Biol. 7, 675-680 (1989); Eur. J. Nucl. Med. 16, 541 (1990); Eur. J. Nucl. Med. 20, 661-666 (1993) and Eur. J. Nucl. Med. 22, 1163-1172 (1995) all report attempts to stabilise $^{99m}$Tc-HMPAO by the addition of either: gentisic acid, sodium decahydroxypyrophosphate, methylene blue, cobalt chloride or the like. In particular, the post-radiolabelling addition of methylene blue improves the Rcp of $^{99m}$Tc-HMPAO to at least 80% at 4 hours post reconstitution. Similarly, the post-radiolabelling addition of cobalt chloride has been found to improve the Rcp of $^{99m}$Tc-HMPAO at 6 hours post reconstitution to at least 80%.

The stabilisation mechanisms of $^{99m}$Tc-HMPAO by methylene blue and cobalt chloride are believed to be essentially the same. Both are in redox equilibrium in solution, and oxidise excess tin(II), thus stabilising $^{99m}$Tc-HMPAO. However, when the reducing tin(II) and methylene blue or cobalt chloride coexist in solution before the Tc-99m radiolabelling step, the tin(II) reductant is completely oxidised, so that the Tc-99m labelling becomes impossible because there is no longer any reducing agent present to reduce the Tc(VII) $^{99m}$Tc-blue or cobalt chloride is used as a stabiliser for $^{99m}$Tc-HMPAO, it must be added after the Tc-99m radiolabelling step and cannot be pre-mixed with the ligand (HMPAO) and $^{99m}$Tc-pertechnetate. Accordingly, any kit for the preparation of $^{99m}$Tc-HMPAO employing such stabilisers, must be composed of two vials (referred to hereinafter as a 2-vial kit). One vial is a freeze-dried vial containing the HMPAO ligand together with the tin(II) reductant and other excipients. The other is a vial containing the stabiliser (methylene blue or cobalt chloride). Thus, the most successful prior art methods of stabilising $^{99m}$Tc-HMPAO to date all require the use of 2-vial kits.

When the kit for preparing $^{99m}$Tc-HMPAO is a 2-vial kit, the radiolabelling operation is more complicated than for a single vial kit and comprises two steps:
(1) $^{99m}$Tc-pertechnetate solution is added to the vial containing the HMPAO ligand and the resulting mixture is mixed by shaking;
(2) a stabiliser solution from the second vial (eg. methylene blue or cobalt chloride) is added to the reconstituted mixture from step (1) in the first vial.

It is necessary that the time between the first and second steps is controlled so as to be as close as possible to two minutes. Too short a time, and $^{99m}$Tc-HMPAO complex formation may be incomplete and hence addition of the stabiliser may adversely affect the Rcp by oxidising the stannous ion before the reduction of the pertechnetate starting material is complete. Too long a time, and the stabilising effect is delayed. In such a procedure it is also necessary that care be taken with respect to the amounts of the solutions added. The operator must also take due care to ensure that the vials are not inadvertently mixed up at any stage. In addition, there is an increased risk of radiation dose to the operator due to the increased number of manipulations. Moreover, when methylene blue is added to $^{99m}$Tc-HMPAO, a precipitate is produced, so that a filtration step becomes necessary, and thus the procedure becomes more complicated.

There is therefore a need for a single vial kit for the preparation of $^{99m}$Tc-HMPAO which has both shelf-life and post-radiolabelling stability. The present invention provides a kit which solves this problem, and is straightforward to use.
The Present Invention.

The present invention relates to a stabiliser for radiopharmaceuticals which comprises a combination of an amino-substituted aromatic carboxylic acid or a salt, ester or amide thereof, with a diphosphonic acid or a salt thereof with the proviso that the radiopharmaceutical is not a metal complex of the diphosphonic acid.

DETAILED DESCRIPTION OF THE INVENTION

In a first aspect, the present invention provides:
a stabilised radiopharmaceutical composition which comprises:
(i) a radiopharmaceutical;
(ii) an amino-substituted aromatic carboxylic acid or a salt, ester or amide thereof;
(iii) a diphosphonic acid or salt thereof,
with the proviso that the radiopharmaceutical is not a metal complex of the diphosphonic acid.

By the term 'amino-substituted aromatic carboxylic acid' is meant a compound in which at least one hydrogen atom on the aromatic ring of an aromatic carboxylic acid is substituted with at least one amino group. The aromatic group is preferably benzene. Preferred amino-substituted aromatic carboxylic acids are: 2-aminobenzoic acid, 3-aminobenzoic acid, 4-aminobenzoic acid (pABA), 3,5-diaminobenzoic acid and 4-aminosalicylic acid. 4-aminobenzoic acid (pABA) is especially preferred.

The salt of the amino-substituted aromatic carboxylic acid is suitably a salt with a biocompatible cation. By the term "biocompatible cation" is meant a positively charged counterion which forms a salt with an ionised, negatively charged group (here a carboxylate group), where said positively charged counterion is also non-toxic and hence suitable for administration to the mammalian body, especially the human body. Examples of suitable biocompatible cations include: the alkali metals (eg. sodium or potassium); the alkaline earth metals (eg. calcium, magnesium and barium); and the ammonium ion. A preferred biocompatible cation is sodium. Preferred salts of the present invention include: sodium 2-aminobenzoate, sodium 3-aminobenzoate, sodium 4-aminobenzoate (NapABA), sodium 3,5-diaminobenzoate, sodium 4-aminosalicylate, potassium 2-aminobenzoate, potassium 3-aminobenzoate, potassium 4-aminobenzoate, potassium 3,5-diaminobenzoate and potassium 4-aminosalicylate. Sodium 4-aminobenzoate (NapABA) is especially preferred.

Suitable esters of the aromatic carboxylic acid include methyl, ethyl or propyl esters. Preferred esters are: methyl 2-aminobenzoate, methyl 3-aminobenzoate, methyl 4-aminobenzoate, methyl 3,5-diaminobenzoate, methyl 4-aminosalicylate, ethyl 2-aminobenzoate, ethyl 3-aminobenzoate, ethyl 4-aminobenzoate, ethyl 3,5-diaminobenzoate, ethyl 4-aminosalicylate, propyl 2-aminobenzoate, propyl 3-aminobenzoate, propyl 4-aminobenzoate, propyl 3,5-diaminobenzoate and propyl 4-aminosalicylate.

Suitable amides of the amino-substituted aromatic carboxylic acid are amides formed by derivatising the carboxyl group of the aromatic carboxylic acid with either ammonia or a compound having at least one amino group, and include such compounds as 2-aminobenzamide, 3-aminobenzamide and 4-aminobenzamide.

The diphosphonic acid of the present invention is suitably a 1,1- or a 1,2-diphosphonic acid, or a diphosphonic acid derivative of an amine such as ethylenediaminetetraphosphonic acid (EDTMP). 1,1-diphosphonic acids are preferred, such as methylenediphosphonic acid (MDP), hydroxymethanediphosphonic acid (HMDP), hydroxyethanediphosphonic acid (HEDP). Methylenediphosphonic acid (MDP) and hydroxymethanediphosphonic acid (HMDP) are especially preferred. Suitable salts of the diphosphonic acid are with a 'biocompatible cation' as defined above. Preferred such diphosphonate salts include: sodium methylenediphosphonate, sodium hydroxymethanediphosphonate, sodium hydroxyethanediphosphonate, sodium ethylenediamine-tetraphosphonate, ammonium methylenediphosphonate, ammonium hydroxymethanediphosphonate, ammonium hydroxyethanediphosphonate and ammonium ethylenediamine-tetraphosphonate.

The combination of compounds in the stabiliser for radiopharmaceuticals of the present invention is preferably a combination of sodium 4-aminobenzoate (NapABA) with methylenediphosphonic acid (MDP) or hydroxymethanediphosphonic acid (HMDP).

Without wishing to be bound by theory, it is believed that the stabilisers of the present invention act as follows:

The amino-substituted aromatic carboxylic acid or its salt, ester or amide has a reducing ability and removes any oxidising free radicals which result from the radiolysis of the solution, and hence inhibits the oxidative destruction of the radiopharmaceutical by free radical attack. On the other hand, when excess tin(II) reductant remains after completion of the radiolabelling, the diphosphonic acid or its salt inhibits the excess stannous ion from reductively degrading the radiopharmaceutical. It is a surprising finding of the present invention that such stabilisers can be present in a single step radiopharmaceutical preparation without either:

(i) preventing or hindering the stannous reduction of the radiopharmaceutical precursor, with consequent adverse effect on Rcp;
(ii) complexing with the radiometal to form undesirable radioactive impurities (eg. diphosphonic acid complexes of the radionuclide).

Accordingly, the amount of the diphosphonic acid or its salt to be added to the radiopharmaceutical depends upon the amount of the reducing tin(II) contained in the radiopharmaceutical preparation or kit. The amount of the diphosphonic acid or its salt effective to stabilise the radiopharmaceutical is 1 to 10 moles per mole of stannous, preferably 2 to 8 moles per mole of stannous, most preferably 4 to 6 moles per mole of stannous.

The radionuclide of the radiopharmaceutical of the present invention is a γ-ray or β-ray emitter, preferably Tc-99m, Re-186 or Re-188, most preferably Tc-99m. γ-ray emitters are mainly used for radiodiagnosis and β-ray emitters are mainly used for radiotherapy.

When a radiodiagnostic radiopharmaceutical of this invention is intracorporeally administered to a human being, the level of radioactivity used is in the range of from 370 to 1,480 MBq, preferably from 370 to 1,110 MBq. When a radiotherapeutic agent of the radiopharmaceuticals of this invention is intracorporeally administered to a human being, the radioactivity level is in the range of from 37 to 18,500 MBq, preferably from 370 to 7,400 MBq.

The radiopharmaceutical comprises an active ingredient which is susceptible to either degradation by the reducing action of the reductant (present to help effect labelling of the radionuclide), or radiolysis. By using the stabiliser composition of the present invention to stabilise such active ingredients, it is possible to prolong the useful lifetime post-radiolabelling to at least twice that of the prior art. The stabilisers of the present invention are particularly useful when the active ingredient comprises a ligand having a tetradentate diaminedioxime donor set, especially d,l-hexamethylpropyleneamine oxime or HMPAO (exametazime), 4,9-diaza-3,3,10,10-tetramethyldodecane-2,11-dione dioxime (PnAO), and similar compounds.

In a second aspect, the present invention provides a non-radioactive kit for the preparation of the stabilised radiopharmaceutical composition described above which comprises:
(i) an amino-substituted aromatic carboxylic acid or a salt, ester or amide thereof;

(ii) a diphosphonic acid or salt thereof,
with the proviso that the radiopharmaceutical is not a metal complex of the diphosphonic acid.

Thus, the stabiliser for radiopharmaceuticals of the present invention can be pre-mixed with the ligand prior to radiolabelling, so that the formulation of a single vial, non-radioactive kit for the preparation of a stabilised radiopharmaceutical (which is not a radionuclide complex of the diphosphonic acid stabilizer) is possible. This simplifies the labelling procedure of the prior art 2-vial kit, shortens the labelling time and diminishes the risk of operator exposure to harmful radiation. The single vial kit of the present invention also has an extended stability post radioactive preparation, which in turn extends the useful lifetime for the user of the kit, eg. a clinician.

Suitable non-radioactive kits of the present invention comprise 0.01 to 10 mg of an amino-substituted aromatic carboxylic acid or its salt, ester or amide, and 0.01 to 1 mg of a diphosphonic acid or its salt. When the kit contains stannous, the amount of the diphosphonic acid or its salt effective to stabilise is 1 to 10 moles per mole of stannous. Preferably, the ratio of diphosphonic acid or its salt is 2 to 8 moles per mole of stannous, most preferably 4 to 6 moles per mole of stannous.

In a third aspect, the present invention discloses the use of a diphosphonic acid or a salt thereof as a stabiliser for radiopharmaceuticals, with the proviso that the radiopharmaceutical is not a metal complex of the diphosphonic acid suitable diphosphonic acid salts are those with a biocompatible cation as described above. Preferably the radiopharmaceutical also comprises stannous in the formulation. Most preferably, the radiopharmaceutical comprises $^{99m}$Tc. Preferably, the diphosphonic acid or salt thereof used as a stabiliser is methylenediphosphonic acid (MDP), hydroxymethanediphosphonic acid (HMDP), hydroxyethanediphosphonic acid (HEDP), ethylenediaminetetraphosphonic acid (EDTMP), and salts thereof.

In a fourth aspect, the present invention discloses the use of a diphosphonic acid or a salt thereof as a stabiliser for non-radioactive kits for the preparation of radiopharmaceuticals, with the proviso that the radiopharmaceutical is not a metal complex of the diphosphonic acid. Suitable diphosphonic acid salts are those with a biocompatible cation as described above. Preferably the non-radioactive kit further comprises stannous in the formulation. Most preferably, the non-radioactive kit is for the preparation of a $^{99m}$Tc radiopharmaceutical. Preferably, the diphosphonic acid or salt thereof used as a stabiliser is methylenediphosphonic acid (MDP), hydroxymethanediphosphonic acid (HMDP), hydroxyethanediphosphonic acid (HEDP), ethylenediaminetetraphosphonic acid (EDTMP), and salts thereof.

DESCRIPTION OF THE DRAWINGS

FIG. 1 compares the change in Rcp of $^{99m}$Tc-HMPAO prepared from Composition III, Composition III+lactose and a commercially available kit for preparing $^{99m}$Tc-HMPAO, each of which had been stored for 6 months prior to reconstitution.

The present invention is explained in more detail with reference to the following Examples:

Example 1 is a comparative example for a two step process (including prior art stabilisers such as cobalt chloride). An Rcp of $^{99m}$Tc-HMPAO of at least 80% 3 hours after the addition is judged as effective stabilisation. However, as is clear from Table 1, the only single stabiliser which meets this criterion is cobalt chloride.

Example 2 shows that $^{99m}$Tc-HMPAO can be effectively stabilised in a single-step process, using a mixture of two compounds as stabilisers, and that the stability is significantly increased over that achieved using the 2-step process of Example 1.

Example 3 provides further data on optimising the combinations of MDP/NapABA and HMDP/NapABA in a single step process. The molar ratio of Sn$^{2+}$ to MDP/HMDP was kept constant (1:5), and the amounts added were varied.

Example 4 shows that lyophilised non-radioactive kits for the preparation of $^{99m}$Tc radiopharmaceuticals can be prepared using the compositions of the present invention. Lactose (a known cryoprotectant excipient in freeze-dried formulations), is shown to be useful to preserve stannous levels for extended shelf-life periods.

Example 5 shows that the combination HMDP/NapABA is also effective as a stabiliser for $^{99m}$Tc-HMPAO.

Example 6 provides data on the stannous or tin(II) content of the freeze-dried kits, as a function of shelf-life storage in the dark at 4° C., and shows that the amount of reducing tin(II) in Composition III+lactose is higher than that in Composition III. Moreover, the amount of the reducing tin(II) in Composition III shows some tendency to decrease with increasing storage time. Accordingly, when the freeze-dried kit is stored for a prolonged period of time, lactose may be used in the kit composition to maintain the amount of the tin(II) reductant constant.

Example 7 compares the Rcp after 6-months storage of the freeze-dried kits of the present invention, with the Rcp for $^{99m}$Tc-HMPAO prepared from a commercially available kit. The Rcp decreases as a function of time post-reconstitution for the commercial kit, but for Composition III and Composition III+lactose, the Rcp's at 6 hours post-reconstitution were at least 80%. This shows that, whilst the stannous levels without lactose do show some modest decrease (Example 5), the decrease does not impair the performance of the kit.

Example 8 shows that freeze-dried kits containing the stabiliser composition HMDP/NapABA have an effective shelf-life.

Example 9 compares the biodistribution in rats of $^{99m}$Tc-HMPAO prepared using kit Composition III and kit Composition III+lactose of the present invention, with a commercial $^{99m}$Tc-HMPAO kit preparation. No significant difference in uptake in target organs was found. This includes the brain, which is the diagnostic imaging application of the present commercial $^{99m}$Tc-HMPAO agent. These results show that the added compounds (MDP, NapABA and lactose), which are not present in the commercially available kit, do not adversely affect the biological behaviour of the $^{99m}$Tc radiopharmaceutical.

Example 10 describes various lyophilisation methods suitable for freeze-dried kit preparation of formulations of the present invention.

Example 11 compares the Rcp of the various freeze-dried kits of Example 10.

Example 1

The Rcp of $^{99m}$Tc-HMPAO Using a Single Stabiliser: Two Step Process (Comparative Example)

The radiochemical purity (Rcp) of $^{99m}$Tc-HMPAO prepared using a commercially available kit (CERETEC™) for preparing $^{99m}$Tc-HMPAO is 80% at one hour post-reconstitution, and the Rcp decreases thereafter with time. On the other hand, in the case of $^{99m}$Tc-HMPAO stabilised with cobalt chloride, the Rcp 6 hours after radiolabelling is 80%. The following known medically acceptable compounds and additives were studied: ascorbic acid, sodium ascorbate, gentisic acid, gentisic acid ethanolamide, methylenediphosphonic acid (MDP), succinic acid, 4-aminobenzoic acid (pABA) and sodium 4-aminobenzoate (NapABA).

To each of ten vials each containing 0.5 mg of HMPAO and 4.0 μg of $Sn^{2+}$ (stannous), was added sodium pertechnetate (1.48 GBq in 5 ml of saline) to carry out the radiolabelling. To each of 9 of the ten reconstituted vials was individually added the compound shown in Table 1 at a time of 2 minutes post-radiolabelling. Nothing was added to the remaining vial. At 1 minute and 3 hours after the addition, an aliquot was taken from each vial and the Rcp measured by a combination of three chromatographic systems (stationary phase/developing solvent: silica gel/methyl ethyl ketone, silica gel/saline, filter paper/50% aqueous acetonitrile). The results are given in Table 1:

TABLE 1

Radiochemical purity (Rcp) of $^{99m}$Tc-HMPAO after the addition of a single stabiliser (%, n = 3).

| Name of Additive (amount) | Rcp 1 min from addition (%) | Rcp 3 hours from addition (%) |
|---|---|---|
| No additive | 87 ± 4 | 38 ± 15 |
| Cobalt chloride (200 μg) | 94 ± 3 | 89 ± 2 |
| Ascorbic acid (4.5 μg) | 83* | 41* |
| Sodium ascorbate (10 mg) | 90* | 51* |
| Gentisic acid (30 μg) | 87 ± 2 | 77 ± 3 |
| Gentisic acid ethanolamide (30 μg) | 61 ± 3 | 29 ± 13 |
| Methylene diphosphonic acid (10 μg) | 79* | 30* |
| 4-Aminobenzoic acid (30 μg) | 80 ± 8 | 67 ± 5 |
| Sodium 4-amino-benzoate (30 μg) | 69 ± 5 | 39 ± 11 |
| Succinic acid (30 μg) | 51* | 14* |

Note:
*n = 1

Example 2

Examination of Stabilisation of $^{99m}$Tc-HMPAO by a Combination of Two Compounds: Single Step Process The combinations studied were:

(i) ascorbic acid and hydroxymethanediphosphonic acid (HMDP);

(ii) sodium 4-aminobenzoate (NapABA) and methylenediphosphonic acid (MDP).

A composition comprising 0.5 mg of HMPAO, 4.0 μg of $Sn^{2+}$, 1.0 μg of HMDP and 0.5 μg of ascorbic acid (Composition A), and a composition comprising 0.5 mg of HMPAO, 5.4 μg of $Sn^{2+}$, 40.5 μg of MDP and 0.5 mg of NapABA (Composition B) were prepared. To each of A and B was added sodium pertechnetate (1.48 GBq in 5 ml) to carry out the labelling. After 3 hours, an aliquot was taken from each, and the Rcp measured by a combination of three chromatographic systems (stationary phase/developing solvent: silica gel/methyl ethyl ketone, silica gel/saline, filter paper/50% aqueous acetonitrile).

The Rcp of $^{99m}$Tc-HMPAO 3 hours after Tc-99m labelling was about 62% in the case of Composition A and about 80% in the case of Composition B.

Example 3

Optimisation of Stabiliser Composition: Single Step Process

As shown in Table 2, six different sample compositions were prepared and stored in the dark at 4° C. One vial of each formulation was taken out at each time point (1, 7, 31 and 32-days storage), and sodium pertechnetate (1.48 GBq in 5 ml) was added. At 6 hours post addition of pertechnetate, an aliquot was taken from each vial and the Rcp measured by a combination of three chromatographic systems (stationary phase/developing solvent: silica gel/methyl ethyl ketone, silica gel/saline, filter paper/50% aqueous acetonitrile). The results are shown in Table 2:

TABLE 2

Sample Compositions and Rcp of $^{99m}$Tc-HMPAO 6 hours post-radiolabelling (n = 1, *n = 3).

| | | Composition | | | | | |
|---|---|---|---|---|---|---|---|
| | | I | II | III | IV | V | VI |
| Preparation Conditions | HMPAO (mg) | 0.5 | 0.5 | 0.5 | 0.5 | 0.5 | 0.5 |
| | NapABA | 0.5 | 0.1 | 0.1 | 0.1 | 0.5 | — |
| | $Sn^{2+}$ (μg) | 5.4 | 5.4 | 8.1 | 8.1 | 8.1 | 8.1 |
| | MDP (μg) | 40.5 | 40.5 | 61.0 | 61.0 | — | — |
| | HMPD (μg) | — | — | — | — | 66.0 | 66.0 |
| Rcp (%) - after storage time | 1 day | 86.4 | 79.5 | 82.2 | 73.8 | 84.8 ± 2.7* | 77.3 ± 5.5* |
| | 7 days | 80.8 | 80.9 | 82.1 | 81.1 | — | — |
| | 32 days | 79.0 | 81.8 | 84.3 | 66.5 | — | — |
| | 31 days | — | — | — | — | 83.5 ± 2.2* | 72.0 ± 0.2* |

Note:
*n = 3.

Compositions II, III and V show that, even in the case of samples stored for 32 days in the dark at 4° C., the Rcp at 6 hours post-reconstitution was at least 80%. Compositions III and V, which exhibited a higher Rcp, were therefore used as the basis for subsequent tests.

Example 4

Stabilisation of $^{99m}$Tc-HMPAO by a Combination of MDP and NapABA: Single Step Process using a Freeze-Dried Kit Composition III of Example 3, and a composition prepared by adding lactose to Composition III (referred to hereinafter as Composition III+lactose) were used to prepare four lots of freeze-dried kit in each case. The amounts of compounds shown below correspond to the scale for a production batch of about 100 freeze-dried kit vials.

First, anhydrous stannous chloride (25.8 mg) and MDP (122 mg) were dissolved in 0.1 M hydrochloric acid (1,000 ml). The resulting solution is referred to hereinafter as Solution 1. d,l-HMPAO (100 mg) and NapABA (100 mg) were dissolved in Solution 1 (100 ml), to give a solution referred to hereinafter as Solution 2. Solution 2 was divided into two 50 ml portions, one of which was adjusted to a pH of 8.5-9.0 with sodium hydroxide and thereafter the total volume was adjusted to 10.0 ml with water by use of a measuring cylinder. In the other 50 ml portion was dissolved 300 mg of lactose monohydrate, the resulting solution was adjusted to a pH of 8.5 to 9.0 with sodium hydroxide, and thereafter, the total volume was adjusted to 100 ml with water by use of a measuring cylinder. 1.0 ml of each of the solutions obtained was placed in each vial, which was then frozen at −50 to −78° C. and then freeze-dried for about 24 hours. After completion of the freeze-drying, the vials were sealed and the freeze-dried kit was stored in the dark at 4° C. The same procedure was repeated four times to prepare four separate lots of each of, Composition III and Composition III+lactose. Lot Nos. ID-01 to ID-04 were of Composition III and Lot Nos. ID-05 to ID-08 were of Composition III+lactose. The production conditions and results of each lot are shown in Table 3.

TABLE 3

Production conditions and results of each lot

| Lot No. | pH before freezing | Freezing temperature (° C.) | Number of Vials Produced | Property[#] |
|---|---|---|---|---|
| ID-01 | 9.0 | −50 | 99 | Fair |
| ID-02 | 9.0 | −78 | 90 | Bad |
| ID-03 | 8.5 | −78 | 39 | Bad |
| ID-04 | 9.0 | −50 | 99 | Fair |
| ID-05 | 9.0 | −50 | 91 | Good |
| ID-06 | 9.0 | −78 | 92 | Good |
| ID-07 | 8.5 | −78 | 94 | Good |
| ID-08 | 8.5 | −50 | 91 | Good |

[#]where 'property' refers to the behaviour during lyophilisation:
Good = the cake in the freeze-dried kits kept well-formed;
Fair = the cake in the freeze-dried kits was partly broken, but there was no loss of powder from the vials during lyophilisation;
Bad = the cake in the freeze-dried kits was completely broken, and some of the powder was lost from the vials during lyophilisation.

In all the lots other than ID-03 (which is of Composition III), at least 90 vials were produced. Among the four lots of Composition III, only ID-03 was adjusted to a pH of 8.5 before freezing. Moreover, in the case of Composition III+ lactose, even when the pH was adjusted to 8.5 before freezing (ID-07, ID-08), at least 90 vials could be produced. Accordingly, when a freeze-dried kit is produced, it is desirable to adjust the pH to 9.0 in the case of lactose-free Composition III.

Example 5

Stabilisation of $^{99m}$Tc-HMPAO by a Combination of HMDP and NapABA: Single Step Process using a Freeze-Dried Kit Composition V of Example 3, and a composition prepared by adding lactose to Composition V (referred to hereinafter as Composition V+lactose) were used to prepare one lot of freeze-dried kits in each case. The freeze-dried kits were prepared in much the same manner as that of Example 4, except that Solution 1 was slightly different—in this case anhydrous stannous chloride (25.8 mg) and HMDP-2Na (132.0 mg) were dissolved in 0.1M hydrochloric acid (1,000 mL). Lot Nos. ID-09 was of Composition V and Lot Nos. ID-10 was of Composition V+lactose. The production conditions and results of each lot are shown in Table 4.

TABLE 4

Production conditions and results of each lot.

| | pH before freezing | Freezing Temperature (° C.) | Number of Vials Produced | Property[#] |
|---|---|---|---|---|
| ID-09 | 8.8 | −50° C. | 49 | Fair |
| ID-10 | 8.8 | −50° C. | 45 | Good |

[#]defined in Example 4.

Example 6

Determination of the Amount of tin(II) in the Freeze-Dried Kit as a Function of Storage Time Vials of Composition III (ID-01, O₂, 03 and 04), Composition III+lactose (ID-05, 06, 07 and 08), Composition V (ID-09) and Composition V+lactose (ID-10) which had been stored in the dark at 4° C. for periods of 1 day, 3-months and 6-months, were allowed to warm to room temperature. The amount of tin(II) was then determined by an absorbance method. The results obtained are shown in Table 5.

TABLE 5

Amounts of reducing tin(II) determined (μg/vial, n = 2).

| | 1-day storage | 3-month storage | 6-month storage |
|---|---|---|---|
| Composition III | 9.5 ± 0.2 | 9.1 ± 0.5 | 8.7 ± 0.5 |
| Composition III + lactose | 10.3 ± 0.5 | 10.5 ± 0.5 | 10.8 ± 0.4 |
| Composition V | 10.1 ± 0.0 | — | — |
| Composition V + lactose | 10.3 ± 0.3 | — | — |

Note:
Each value was an average value of 4 lots.

Example 7

Radiochemical Purity of Freeze-Dried Kits Containing MDP and NapABA Studied over a 6-Month Shelf-Life Storage Period Four lots of each of Composition III and Composition III+lactose produced in Example 4 were subjected to examination of radiochemical purity after 6-months storage in the dark at 4° C.

Vials of freeze-dried Composition III (ID-01, $O_2$, 03 and 04) and Composition III+lactose (ID-OS, 06, 07 and 08) were stored for 6 months in the dark at 4° C. After a storage period of 1 day, 1, 3 and 6 months, the vials were allowed to warm to room temperature, and Tc-99m labelling was carried out. Thus, to one vial of each lot was added sodium pertechnetate (1.48 GBq in 5 ml). Aliquots were taken after times of 2 minutes, one hour, 3 hours and 6 hours and the Rcp was measured by a combination of three chromatographic systems (stationary phase/developing solvent: silica gel/methyl ethyl ketone, silica gel/saline and filter paper/50% aqueous acetonitrile). The results obtained at 6 hours are shown in Table 6. When Composition III and Composition III+lactose were radiolabelled after 6-month shelf-life storage, simultaneously, sodium pertechnetate (1.48 GBq/5 ml) was added to a commercially available kit for preparing $^{99m}$Tc-HMPAO (containing 0.5 mg of HMPAO and 4.0 μg of $Sn^{2+}$) as a control. An aliquot thereof was taken after times of one minute, one hour, 3 hours and 6 hours, and then the Rcp was measured in the same manner. The results obtained are shown in FIG. 1.

TABLE 6

Rcp of $^{99m}$Tc-HMPAO at 6 hr post reconstitution by a combination of MDP and NapABA as a function of storage time.

| | | STORAGE PERIOD | | | |
|---|---|---|---|---|---|
| | | 1-day | 1-month | 3-months | 6-months |
| Rcp (%) | Composition III | 86.4 ± 2.2 | 87.4 ± 1.5 | 86.5 ± 2.7 | 88.4 ± 3.4 |
| | Composition III + Lactose | 86.2 ± 2.3 | 86.2 ± 2.4 | 87.9 ± 2.6 | 85.6 ± 2.7 |

Example 8

Radiochemical Purity of Freeze-Dried Kits Containing HMDP and NapABA for 1-Month Shelf-Life Storage One lot of each of Composition V and Composition V+lactose produced in Example 5 were subjected to examination of radiochemical purity for 1-month storage in the dark at 4° C. The Rcp was measured in the same manner. The results obtained are shown in Table 7.

TABLE 7

Rcp of $^{99m}$Tc-HMPAO at 6 hr post-reconstitution stabilised by a combination of HMDP and NapABA as a function of storage time.

| | | Storage Time | |
|---|---|---|---|
| | | 1-day | 1-month |
| Rcp (%) | Composition V | 84.8 ± 2.7 | 83.5 ± 2.2 |
| | Composition V + Lactose | 87.3 ± 2.8 | 86.0 ± 1.0 |

Example 9

Biodistribution in the Rat

To one vial of each of Composition III (ID-$O_2$) and Composition III+lactose (ID-06) obtained in Example 4 was added sodium pertechnetate in a proportion of 1.48 GBq/5 ml to carry out the radiolabelling. After 2 hours, 3.0 to 3.7 MBq of the reconstituted solution was administered to a female Sprague-Dawley strain rat (body weight 140-170 g) which had been previously anaesthetised with sodium thiopentobarbital in the tail vein. At one hour post-administration, the animal was sacrificed and the radioactivity in each organ was measured using a NaI single channel analyser. Separately, sodium pertechnetate was added in a proportion of 1.48 GBq/5 ml to the commercially available kit for preparing $^{99m}$Tc-HMPAO. In the same manner, at 15 minutes post-reconstitution, 3.0-3.7 MBq of the solution was administered to the same kind of rat, and the biodistribution of radioactivity in each organ measured. The results obtained are shown in Table 8:

TABLE 8

Biodistribution of Commercial $^{99m}$Tc-HMPAO, Composition III (ID-02) and Composition III + lactose (ID-06) in the female rat at one hour post administration (upper row: % ID/organ, lower row: % ID/g, n = 5).

| | Commercial $^{99m}$Tc-HMPAO | Composition III (ID-02) | Composition III + lactose (ID-06) |
|---|---|---|---|
| Brain | 1.66 ± 0.13 | 1.65 ± 0.10 | 1.73 ± 0.15 |
| | 0.96 ± 0.07 | 0.96 ± 0.15 | 1.01 ± 0.07 |
| Blood | 15.38 ± 0.72 | 14.41 ± 1.68 | 14.07 ± 1.51 |
| | 1.56 ± 0.04 | 1.64 ± 0.06 | 1.45 ± 0.18 |
| Heart | 0.81 ± 0.04 | 0.85 ± 0.03 | 0.90 ± 0.10 |
| | 1.61 ± 0.08 | 1.75 ± 0.10 | 1.72 ± 0.03 |
| Lung | 3.41 ± 0.20 | 3.15 ± 0.18 | 3.39 ± 0.38 |
| | 4.05 ± 0.28 | 4.26 ± 0.29 | 4.14 ± 0.36 |
| Liver | 5.91 ± 0.20 | 6.49 ± 0.48 | 7.68 ± 0.38 |
| | 1.10 ± 0.07 | 1.36 ± 0.13 | 1.44 ± 0.14 |
| Spleen | 0.78 ± 0.10 | 0.79 ± 0.18 | 0.86 ± 0.12 |
| | 2.17 ± 0.12 | 2.24 ± 0.12 | 2.25 ± 0.21 |
| Kidney | 4.27 ± 0.27 | 5.04 ± 0.48 | 4.81 ± 0.31 |
| | 4.39 ± 0.16 | 4.78 ± 0.64 | 4.46 ± 0.21 |
| Stomach | 1.41 ± 0.54 | 2.15 ± 0.46 | 1.70 ± 0.79 |
| | 0.49 ± 0.17 | 1.24 ± 0.43 | 0.93 ± 0.54 |
| Small Intestine | 17.27 ± 0.85 | 17.61 ± 0.87 | 20.23 ± 1.50 |
| | 2.86 ± 0.17 | 3.47 ± 0.33 | 3.94 ± 0.46 |
| Large Intestine | 2.08 ± 0.25 | 2.14 ± 0.34 | 2.05 ± 0.24 |
| | 0.35 ± 0.03 | 0.40 ± 0.04 | 0.34 ± 0.03 |
| Skin | 0.78 ± 0.61 | 0.68 ± 0.55 | 0.51 ± 0.34 |
| | 0.39 ± 0.04 | 0.37 ± 0.09 | 0.31 ± 0.09 |
| Muscle | 0.91 ± 0.49 | 0.67 ± 0.41 | 0.49 ± 0.21 |
| | 0.28 ± 0.03 | 0.29 ± 0.03 | 0.16 ± 0.02 |

TABLE 8-continued

Biodistribution of Commercial $^{99m}$Tc-HMPAO,
Composition III (ID-02) and Composition III + lactose
(ID-06) in the female rat at one hour post administration
(upper row: % ID/organ, lower row: % ID/g, n = 5).

|  | Commercial $^{99m}$Tc-HMPAO | Composition III (ID-02) | Composition III + lactose (ID-06) |
|---|---|---|---|
| Urine | 12.36 ± 1.18 | 11.78 ± 2.18 | 12.07 ± 1.11 |
| Carcass | 36.96 ± 0.83 | 37.76 ± 2.18 | 33.95 ± 1.37 |
|  | 0.34 ± 0.02 | 0.37 ± 0.02 | 0.31 ± 0.01 |

Example 10

Methods of Freeze-Dried Kit Preparation

The freeze-dried kit (Composition V+lactose of Example 5) was prepared by two methods. The first method (ID-11) was similar to that of Example 5, but with a modified Solution 2—thus, d,l-HMPAO (250 mg), NapABA (250 mg) and lactose monohydrate (1.5 g) were dissolved in Solution 1 (250 mL). The solution was added to water (250 mL) and adjusted to pH 8.9. The production conditions and results for ID-11 are shown in Table 9.

The second method (ID-12) is described below.

Thus, lactose monohydrate (3.03 g), NapABA (505 mg), d,l-HMPAO (505 mg), HMDP (66.6 mg) and anhydrous stannous chloride (13.1 mg) were dissolved in 0.1M hydrochloric acid (1000 mL) in the order given. The solution was then adjusted to pH 9.4. The production conditions and results for ID-12 are shown in Table 9.

TABLE 9

Production conditions and results of each lot

|  | pH before freezing | Freezing Temperature ° (C.) | Number of Vials Produced | Property[#] |
|---|---|---|---|---|
| ID-11 | 8.9 | −40° C. | 290 | Good |
| ID-12 | 9.4 | −40° C. | 240 | Good |

[#]as defined in Example 4.

Example 11

RCP of Freeze-Dried Kits Prepared by Different Methods

The freeze-dried kits in Example 10 were used to examine the RCP. The RCP was measured in the same manner as in Example 7. The results obtained are shown in Table 10.

TABLE 10

Rcp of $^{99m}$Tc-HMPAO at the time after reconstitution

|  | 2 min | 1 hour | 3 hours | 6 hours |
|---|---|---|---|---|
| ID-11 | 90.2 ± 0.4 | 89.3 ± 1.8 | 85.9 ± 1.7 | 85.7 ± 1.7 |
| ID-12 | 87.1 ± 2.1 | 81.4 ± 2.4 | 70.6 ± 1.7 | 60.7 ± 4.0 |

What is claimed is:

1. A stabilized radiopharmaceutical composition which comprises:
   (i) a radiopharmaceutical which is susceptible to either reductive degradation or radiolysis and comprises a metal complex of a radionuclide with a ligand;
   (ii) a tin(II) reductant;
   (iii) a first stabilizer for said radiopharmaceutical which is an amino-substituted aromatic carboxylic acid or a salt, ester or amide thereof;
   (iv) a second stabilizer for said radiopharmaceutical which is a diphosphonic acid or salt thereof, wherein said second stabilizer is present in an amount of 1 to 10 moles per mole of tin(II) reductant,
   wherein the radiopharmaceutical is not a metal complex of the diphosphonic acid.

2. The composition of claim 1, wherein the amino-substituted aromatic carboxylic acid or its salt, ester or amide is selected from the group consisting of 2-aminobenzoic acid, 3-aminobenzoic acid, 4-aminobenzoic acid, 3,5-diaminobenzoic acid, 4-amino-salicylic acid, and salts, esters and amides thereof.

3. The composition of claim 1, wherein the diphosphonic acid or its salt is selected from the group consisting of methylenediphosphonic acid, hydroxymethanediphosphonic acid, hydroxyethanediphosphonic acid, ethylenediaminetetraphosphonic acid, and salts thereof.

4. The composition of claim 1, wherein the amino-substituted aromatic carboxylic acid or salt, ester or amide thereof is sodium 4-aminobenzoate, and the diphosphonic acid is methylenediphosphonic acid.

5. The composition of claim 1, wherein the radiopharmaceutical includes a γ-ray emitter or a β-ray emitter.

6. The composition of claim 5, wherein the radiopharmaceutical includes Tc-99m, Re-186 or Re-188.

7. The composition of claim 1, wherein the ligand is an amine oxime.

8. The composition of claim 7, wherein the amine oxime is selected from the group consisting of d,l-hexamethylpropyleneamine oxime and 4,9-diaza-3,3,10,10-tetramethyldodecane-2,11-dione dioxime.

9. A non-radioactive kit for the preparation of the stabilized radiopharmaceutical composition of claim 1 which comprises:
   (i) a first stabilizer which comprises an amino-substituted aromatic carboxylic acid or a salt, ester or amide thereof; and
   (ii) a second stabilizer which comprises a diphosphonic acid or salt thereof,
   (iii) a ligand capable of forming a metal complex with a radionuclide;
   (iv) a tin(II) reductant, wherein the molar ratio of the diphosphonic acid or its salt to tin(II) is in the range 1 to 10;
   wherein, upon reconstitution with a supply of a metallic radionuclide, said kit provides the desired radiopharmaceutical composition comprising a metal complex of said radionuclide with said ligand,
   and wherein said ligand and said radiopharmaceutical are as defined in claim 1.

10. The kit of claim 9, which includes 0.01 to 10 mg of an amino-substituted aromatic carboxylic acid or its salt, ester or amide, and 0.01 to 1 mg of a diphosphonic acid or its salt.

11. The kit of claim 9, where the ligand is an amine oxime ligand.

12. The kit of claim 11, wherein the amine oxime is selected from the group consisting of d,l-hexamethylpropyleneamine oxime and 4,9-diaza-3,3,10,10-tetramethyldodecane-2,11-dione dioxime.

13. The kit of claim 9, which is lyophilized.

* * * * *